(12) United States Patent
Tanaka et al.

(10) Patent No.: US 11,428,672 B2
(45) Date of Patent: Aug. 30, 2022

(54) COMPONENT-CONCENTRATION MEASURING APPARATUS AND METHOD

(71) Applicant: Nippon Telegraph and Telephone Corporation, Tokyo (JP)

(72) Inventors: Yujiro Tanaka, Tokyo (JP); Takuro Tajima, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 147 days.

(21) Appl. No.: 16/971,770

(22) PCT Filed: Feb. 25, 2019

(86) PCT No.: PCT/JP2019/006966
§ 371 (c)(1),
(2) Date: Aug. 21, 2020

(87) PCT Pub. No.: WO2019/181375
PCT Pub. Date: Sep. 26, 2019

(65) Prior Publication Data
US 2021/0088478 A1 Mar. 25, 2021

(30) Foreign Application Priority Data
Mar. 23, 2018 (JP) .............................. JP2018-055735

(51) Int. Cl.
G01N 29/24 (2006.01)
A61B 5/00 (2006.01)
G01N 33/49 (2006.01)
A61B 5/145 (2006.01)

(52) U.S. Cl.
CPC ....... *G01N 29/2418* (2013.01); *A61B 5/0095* (2013.01); *G01N 33/49* (2013.01); *A61B 5/14532* (2013.01)

(58) Field of Classification Search
CPC .............. G01N 29/2418; G01N 33/49; G01N 2291/02466; G01N 21/00; A61B 5/0095; A61B 5/14532
See application file for complete search history.

(56) References Cited

U.S. PATENT DOCUMENTS 9,995,674 B2 * 6/2018 Prasad .................... G01N 29/46
2011/0118571 A1 * 5/2011 Mandelis ............. A61B 5/0093
250/252.1

FOREIGN PATENT DOCUMENTS

JP 200789662 4/2007

* cited by examiner

*Primary Examiner* — Suman K Nath
(74) *Attorney, Agent, or Firm* — Slater Matsil, LLP

(57) ABSTRACT

A component concentration measurement device includes a light irradiation unit that performs intensity modulation where two lights of wavelengths different from each other are intensity-modulated by signals of a same frequency and a same phase, and a measurement object is irradiated, a detecting unit that detects a photoacoustic wave generated within the measurement object due to irradiation by the light irradiation unit, and converts the detected photoacoustic wave into a first electric signal, and a processing unit that obtains a concentration of a target component contained in the measurement object, on the basis of an amplitude and a phase of the first electric signal. Light absorption coefficients of the two lights, corresponding to a background component contained in the measurement object, are equal in change amount with regard to change in temperature, and have signs different from each other.

12 Claims, 8 Drawing Sheets

COMPONENT-CONCENTRATION MEASURING APPARATUS AND METHOD

CROSS-REFERENCE TO RELATED APPLICATIONS

This application is a national phase entry of PCT Application No. PCT/JP2019/006966, filed on Feb. 25, 2019, which claims priority to Japanese Application No. 2018-055735 filed on Mar. 23, 2018, which applications are hereby incorporated herein by reference.

TECHNICAL FIELD

The present invention relates to a component concentration measurement device and method, and particularly relates to noninvasive measurement technology for component concentration in a living organism

BACKGROUND

As aging of society advances, handling lifestyle diseases is becoming a large problem. Tests for blood sugar level and so forth require blood to be collected, which is a very large burden on patients. Accordingly, noninvasive component concentration measurement devices, where blood is not collected, are being closely watched.

A component concentration measurement device that uses the photoacoustic method has been proposed as a noninvasive component concentration measurement device. In the photoacoustic method, inside of the skin is irradiated by electromagnetic waves, a blood component that is the object of measurement, glucose molecules for example, are made to absorb the electromagnetic waves, eradiation of heat from the glucose molecules causes local thermal expansion, and acoustic waves generated from inside the living organism by the thermal expansion is measured.

However, interaction between glucose and electromagnetic waves is small, and also there is a limit to the intensity of electromagnetic waves by which a living organism can be safely irradiated. Accordingly, sufficient effects have not been attained yet regarding measurement of blood sugar levels in living organisms.

FIG. 7 is a block diagram illustrating a configuration example of a conventional component concentration measurement device 200 that uses the photoacoustic method. A light source that is continuously intensity-modulated is used in this component concentration measurement device 200, and measures the concentration of a target component in a solution where a background component and the target component have been mixed (see PTL 1, for example).

The component concentration measurement device 200 according to a conventional example is configured of a first light source 202, a second light source 203, an oscillator 204, a delay adjuster 205, a first drive circuit 206, a second drive circuit 207, an optical multiplexer 208, an acoustic wave detector 211, a phase detection amplifier 212, a waveform observer 213, a recorder 214, and a 180° phase shifter 215, as illustrated in FIG. 7. The component concentration measurement device 200 uses two light sources, with the first light source 202 generating measurement light of a wavelength $\lambda 1$, and the second light source 203 generates reference light of a wavelength $\lambda 2$.

The oscillator 204 outputs modulation signals for intensity modulation of light output from the first light source 202 and second light source 203.

The delay adjuster 205 delays, out of the signals output from the oscillator 204, signals for driving the second light source 203, by a predetermined amount of time.

The 180° phase shifter 215 inverts and outputs one of the modulation signals output from the oscillator 204. The first drive circuit 206 drives the first light source 202. The second drive circuit 207 drives the second light source 203 on the basis of the modulation signals that have been inverted at the 180° phase shifter 215.

The first light source 202 performs intensity modulation of the measurement light of wavelength $\lambda 1$ under signals from the first drive circuit 206, and outputs the intensity-modulated light. The second light source 203 performs intensity modulation of the reference light of wavelength $\lambda 2$ under signals from the second drive circuit 207, and outputs the intensity-modulated light. Accordingly, the optical multiplexer 208 multiplexes the measurement light and reference light, and electrically performs intensity modulation of each light of the two different wavelengths $\lambda 1$ and $\lambda 2$, by signals of the same frequency and inverse phases, and outputs the intensity-modulated light.

In the conventional component concentration measurement device 200, acoustic waves (photoacoustic waves) are generated within the measurement object by the light of the two of the wavelength $\lambda 1$ and wavelength $\lambda 2$, these photoacoustic waves are detected by the acoustic wave detector 211 that is an acoustic sensor, and are converted into electric signals (photoacoustic signals) proportionate to sound pressure. The photoacoustic signals converted by the phase detection amplifier 212 are then measured.

The difference in intensity between the photoacoustic signals corresponding to the two wavelengths $\lambda 1$ and $\lambda 2$ is measured as electric signals corresponding to the amount of glucose contained in the blood.

Also, regarding the two selected wavelengths in the conventional component concentration measurement device 200, for one wavelength, a wavelength of which a temperature dependency coefficient in an absorbance spectrum of water exhibits a positive tendency, and for the other wavelength, a wavelength of which exhibits a negative tendency, are selected for example, as illustrated in FIG. 8.

In a case where effects of change in absorbance are great, change in absorbance $\Delta \alpha w$ due to change in temperature is found from a known absorbance spectrum by directly measuring the temperature, as illustrated in FIG. 8. Alternatively, change in temperature $\Delta T$ is estimated from change in absorbance of light and $\Delta \alpha w$ is found from a known absorbance spectrum. In this case, $\Delta \alpha = M \alpha g + \Delta \alpha w$ can be written. Accordingly, molar concentration $M = (\Delta \alpha - \Delta \alpha w)/\alpha g$ can be computed and found. Note that $\alpha$ is absorbance, $\alpha w$ is absorbance of water, and $\alpha g$ is absorbance of glucose per molar concentration.

The conventional component concentration measurement device 200 modulates the modulation frequency for electrically performing intensity modulation of each of the two of wavelength $\lambda 1$ and wavelength $\lambda 2$ at the same frequency as a resonant frequency regarding detection of acoustic waves generate at a measurement object, such as a living organism or the like, and thus measures acoustic waves of light of two wavelengths selected taking into consideration nonlinearity regarding an absorption coefficient in measurement values of acoustic waves. Acoustic waves of one wavelength are then normalized from acoustic waves of the difference of the two wavelengths, thereby enabling acoustic waves generated within the measurement object such as a living organism or the like to be detected with higher precision, while eliminating the effects of a great number of parameters regarding which keeping constant is difficult.

CITATION LIST

Patent Literature

PTL 1—Japanese Patent Application Publication No. 2007-89662.

SUMMARY

Technical Problem

However, in the conventional component concentration measurement device described above, the precision of estimation regarding temperature change in components within the living organism that is the object of measurement is not sufficient, and the quantitative precision of the concentration of components within the living organism deteriorates due to the temperature dependency of absorbance of water, which is a background component. Also, the amplitude and phase of photoacoustic signals change due to acoustic resonance within the measurement object, and the quantitative precision of the concentration of components within the living organism deteriorates. Accordingly, there has been a problem with conventional component concentration measurement devices in that quantitative error occurs in the concentration of components within the living organism that are measured.

Embodiments of the present invention has been made to solve the above-described problem, and it is an object thereof to provide a component concentration measurement device and method that can improve quantitative precision in measurement of concentration of components within living organisms.

Means for Solving the Problem

In order to solve the above problem, a component concentration measurement device according to embodiments of the present invention includes a light irradiation unit that performs intensity modulation where two lights of wavelengths different from each other are intensity-modulated by signals of a same frequency and a same phase, and a measurement object is irradiated, a detecting unit that detects a photoacoustic wave generated within the measurement object due to irradiation by the light irradiation unit, and converts the detected photoacoustic wave into a first electric signal, and a processing unit that obtains a concentration of a target component contained in the measurement object, on the basis of an amplitude and a phase of the first electric signal. Light absorption coefficients of the two lights, corresponding to a background component contained in the measurement object, are equal in change amount with regard to change in temperature, and have signs different from each other.

Also, in the component concentration measurement device according to embodiments of the present invention, the light irradiation unit may further irradiate the measurement object by light where the wavelength of one light of the two lights intensity-modulated by signals of the same frequency and the same phase has been shifted by a predetermined change amount, the detecting unit may detect a photoacoustic wave generated within the measurement object due to irradiation by the one light, for each of before and after shifting the wavelength by the predetermined change amount, and convert the detected photoacoustic waves into second electric signals, and the processing unit may normalize the concentration of the target component contained in the measurement object on the basis of the second electric signals.

Also, in the component concentration measurement device according to embodiments of the present invention, the processing unit may calculate a proportionality coefficient for the first electric signal and an optical power of light by which the measurement object is irradiated by the light irradiation unit at each measurement clock time, and normalize the concentration of the target component contained in the measurement object.

Also, in the component concentration measurement device according embodiments of to the present invention, the processing unit may obtain the proportionality coefficient $F(t_i)$ at each measurement clock time $t_i$ using the following Expression $$F(t_i) = \frac{S^{\lambda_1+\Delta\lambda}(t_i) - S^{\lambda_1}(t_i)}{\Delta\alpha I} \qquad \text{Formula 1}$$

where $S^{\lambda_1}$ represents the second electric signal before the wavelength is shifted by the predetermined change amount, $S^{\lambda_1+\Delta\lambda}$ the second electric signal after the wavelength is shifted by the predetermined change amount, $\Delta\alpha I$ change in absorbance, and I the optical power.

Also, in the component concentration measurement device according to embodiments of the present invention, the processing unit may obtain a change $\Delta C(t)$ in concentration of the target component contained in the measurement object, which has been normalized, using the following Expression $$\Delta C(t) = \left(\frac{S_{12}(t_{i+n-1})}{Z(t_{i+n-1})} - \frac{S_{12}(t_i)}{Z(t_i)}\right)\frac{\Delta\alpha}{\gamma_{12}} \propto \left(\frac{S_{12}(t_{i+n-1})}{Z(t_{i+n-1})} - \frac{S_{12}(t_i)}{Z(t_i)}\right) \qquad \text{Formula 2}$$

where $Z = S^{\lambda_1+\Delta\lambda}(t) - S^{\lambda_1}(t)$ and where S12 represents the first electric signal, detected on the basis of the two lights, having been superimposed, and γ12 the temperature absorbance of the measurement object.

Also, in the component concentration measurement device according to embodiments of the present invention, at least one of the two lights is of a wavelength where absorption that the target component exhibits may be maximal.

Also, a component concentration measurement method according to embodiments of the present invention includes a light irradiation step of performing intensity modulation where two lights of wavelengths different from each other are intensity-modulated by signals of a same frequency and a same phase, and a measurement object is irradiated, a detecting step of detecting a photoacoustic wave generated within the measurement object due to irradiation in the light irradiation step, and converting the detected photoacoustic wave into a first electric signal, and a processing step of obtaining a concentration of a target component contained in the measurement object, on the basis of an amplitude and a phase of the first electric signal. Light absorption coefficients of the two lights, corresponding to a background component contained in the measurement object, are equal in change amount with regard to change in temperature, and have signs different from each other.

Also, in the component concentration measurement method according to embodiments of the present invention, in the light irradiation step, the measurement object may be further irradiated by light where the wavelength of one light of the two lights intensity-modulated by signals of the same frequency and the same phase has been shifted by a predetermined change amount, in the detecting step, a photoacoustic wave generated within the measurement object due to irradiation by the one light may be detected, for each of before and after shifting the wavelength by the predetermined change amount, and the detected photoacoustic waves may be converted into second electric signals, and in the processing step, the concentration of the target component contained in the measurement object may be normalized on the basis of the second electric signals.

Effects of Embodiments of the Invention

According to embodiments of the present invention, temperature dependency of the absorbance of the background component is cancelled out, and accordingly quantitative precision can be improved regarding concentration of components within living organisms.

DETAILED DESCRIPTION OF ILLUSTRATIVE EMBODIMENTS

A preferred embodiment of the present invention will be described in detail below, with reference to FIG. 1 to FIG. 8. Also, a case of measuring glucose concentration in blood of a living organism by the component concentration measurement device according to embodiments of the present invention will be described in the following embodiment. Also, components that are common among the drawings are denoted by the same symbols.

Embodiment

Figure 1:
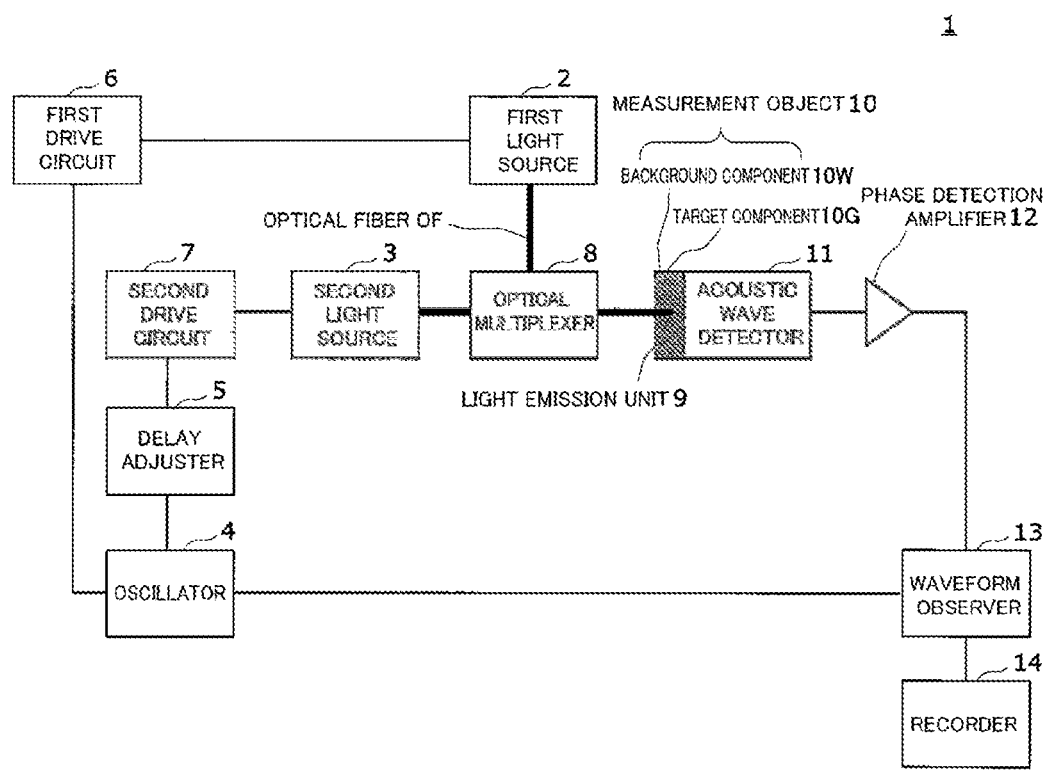
FIG. 1 is a block diagram illustrating a configuration example of a component concentration measurement device according to an embodiment of the present invention.

FIG. 1 is a block diagram illustrating a configuration example of a component concentration measurement device 1 according to an embodiment of the present invention. A feature of the component concentration measurement device 1 is to cancel out thermal dependency of absorbance of water, which is a background component, and to measure the concentration of glucose (target component 10G) of a living organism that is a measurement object 10.

The component concentration measurement device 1 is provided with a first light source 2, a second light source 3, an oscillator 4, a delay adjuster 5, a first drive circuit 6, a second drive circuit 7, an optical multiplexer 8, a light emission unit 9, an acoustic wave detector 11, a phase detection amplifier 12, a waveform observer 13, and a recorder 14.

The measurement object 10 contains water that is a background component 10W, and glucose that is the target component 10G.

The first light source 2, second light source 3, oscillator 4, delay adjuster 5, first drive circuit 6, second drive circuit 7, and optical multiplexer 8 make up a light irradiation unit.

The light irradiation unit irradiates the measurement object 10 by two lights of mutually different wavelengths, which are intensity-modulated by signals of the same frequency and the same phase.

The acoustic wave detector 11 and phase detection amplifier 12 make up a detection unit that detects photoacoustic waves generated within the measurement object 10 due to irradiation by light by the light irradiation unit, and converts the photoacoustic waves into electric signals (photoacoustic signals).

The waveform observer 13 and recorder 14 make up a processing unit that obtains the concentration of the target component 10G contained in the measurement object 10, on the basis of the amplitude and phase of the photoacoustic signals.

Light sources used for the first light source 2 and second light source 3 are light sources where intensity modulation is continuously performed and where the wavelength of one can be changed within an optional range. Solid state laser or semiconductor layer can be used for the first light source 2 and second light source 3. In a case of using the first light source 2 as a variable-wavelength laser for example, there is a method of changing the oscillation frequency by temperature adjustment, a method of using an external resonator, and so forth. When extracting a predetermined wavelength using a solid-state laser, a dispersive element such as a prism, diffractive grating, or the like, can be used.

The oscillator 4 outputs modulation signals for performing intensity modulation of light output from the first light source 2 and second light source 3.

The delay adjuster 5 delays, of the signals output from the oscillator 4, modulation signals for driving the second light source 3, by a predetermined amount of time.

The first drive circuit 6 drives the first light source 2. The first light source 2 performs intensity modulation of measurement light of the wavelength $\lambda 1$, by signals from the first drive circuit 6, and outputs the intensity-modulated measurement light.

The second drive circuit 7 drives the second light source 3 at the same phase as the first light source 2, on the basis of modulation signals output from the delay adjuster 5. The second light source 3 performs intensity modulation of reference light of the wavelength $\lambda 2$, by signals from the second drive circuit 7, and outputs the intensity-modulated reference light.

Accordingly, light of different wavelengths $\lambda 1$ and $\lambda 2$, which has been electrically intensity-modulated by signals of the same frequency and the same phase as each other, is output from the first light source 2 and second light source.

Figure 8:
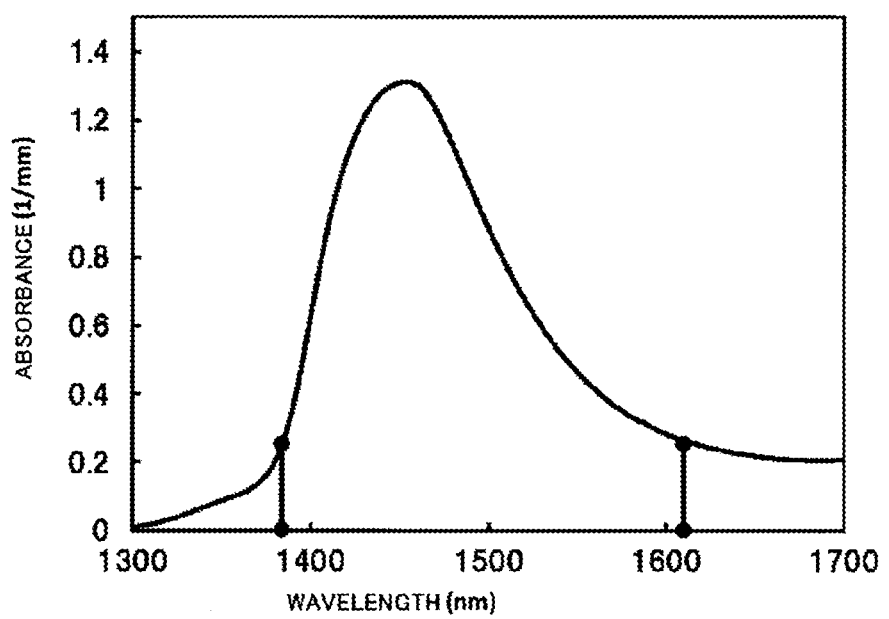
FIG. 8 is an explanatory diagram regarding two wavelengths selected conventionally.

Now, the wavelength $\lambda 1$ of light output from the first light source 2 and the wavelength $\lambda 2$ of light output from the second light source 3 are different wavelengths where absorption exhibited by the background component 10W contained in the measurement object 10 is equal to each other, as described in the conventional selection of two wavelengths (FIG. 8). In the present embodiment, the measurement object 10 is a living organism, and the target component 10G is glucose in the blood, and accordingly absorption exhibited by the background component 10W can be made to be absorption exhibited by water.

Figure 4:
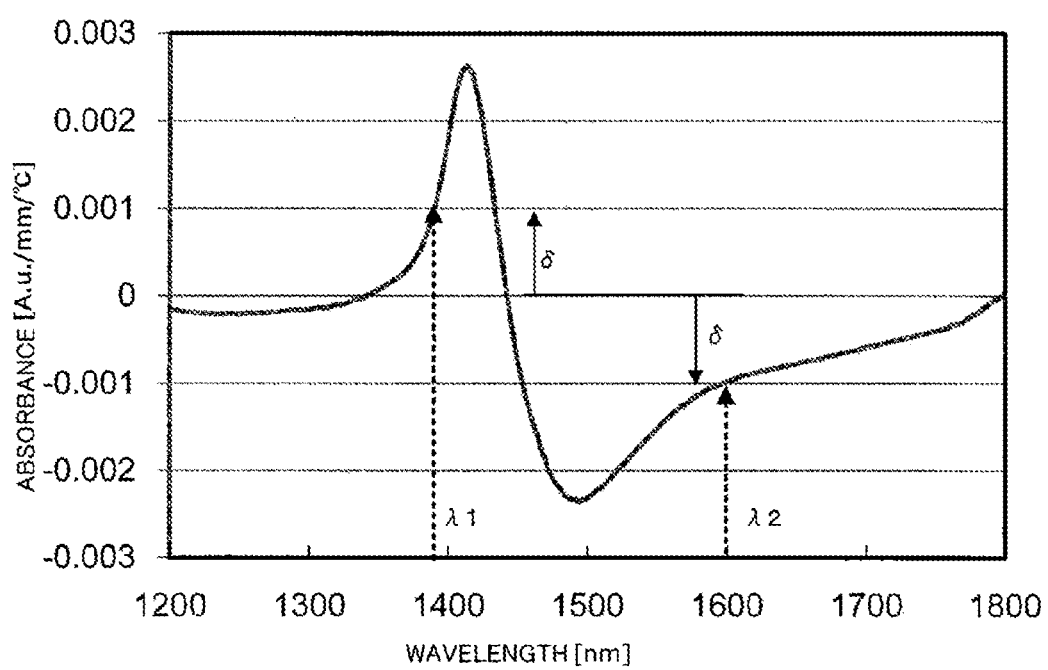
FIG. 4 is a diagram for describing a differential absorption spectrum of glucose.

Contrastively, occurrence of fluctuation in the background component 10W is unavoidable, as shown in temperature-dependent change in absorbance in the absorption spectrum of water in FIG. 4. This is a factor in deterioration of measurement precision of the target component 10G.

In the component concentration measurement device 1 according to the present embodiment, a change amount δ of light absorption coefficient regarding the background component 10W, under change in temperature, is equal in the wavelength λ1 of light output by the first light source 2 and the wavelength λ2 of light output by the second light source 3, but the signs of the light are different from each other, as illustrated in FIG. 4.

Accordingly, if the wavelength λ1 of light and the wavelength λ2 of light are made to be signals of the same phase, the change amount δ of light absorption coefficient regarding the background component 10W under change in temperature can be cancelled out. Further, one of the first light source 2 and second light source 3 preferably is a wavelength where absorption that the target component 10G exhibits is maximal.

Figure 5:
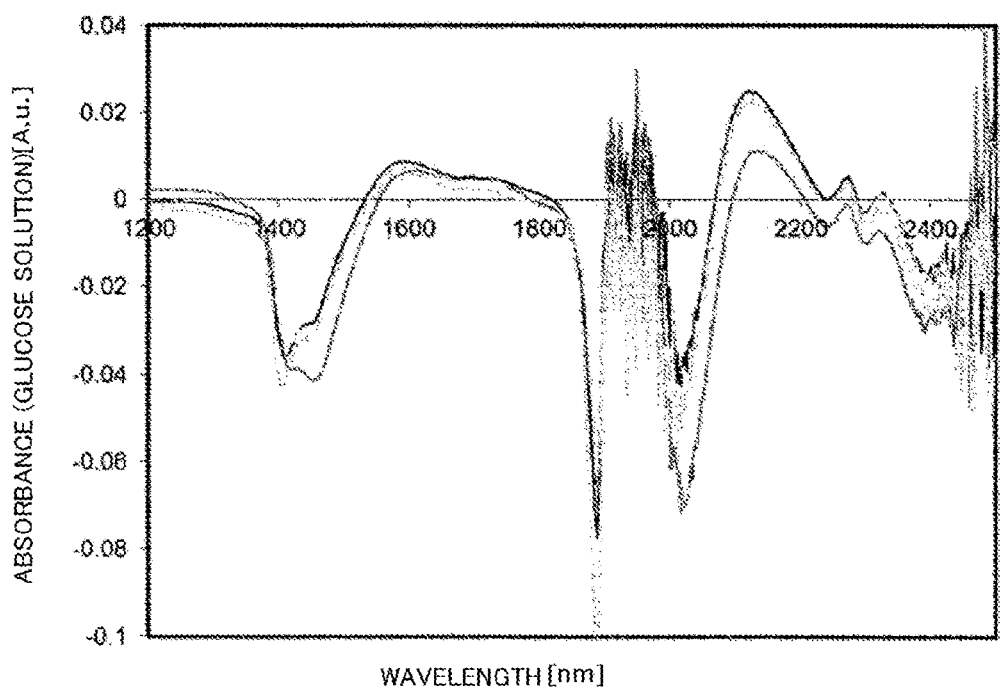
FIG. 5 is a diagram for describing temperature dependency of an absorption spectrum.

The first light source 2 in the present embodiment preferably is of a wavelength of 1600 nm or 2100 nm, which are wavelengths where absorption that glucose exhibits is maximal, as shown in a differential absorption spectrum of glucose in FIG. 5.

In this case, continuous light output by the first light source 2 is measurement light of wavelength λ1 (1400 nm) and continuous light output by the second light source 3 is reference light of wavelength λ2 (1600 nm), for example.

The optical multiplexer 8 multiplexes the light of wavelength λ1 from the first light source 2 and the light of wavelength λ2 from the second light source 3, as illustrated in FIG. 1. The multiplexed light is guided to the light emission unit 9 by an optical fiber OF.

The light emission unit 9 emits the light multiplexed by the optical multiplexer 8 (measurement multiplexed light) toward the measurement object 10. Note that at the light emission unit 9, a right-angle prism, fiber collimator, or ferule may be mounted to the tip of the optical fiber OF depending on the shape of the measurement object 10.

The living organism that is the measurement object 10 generates acoustic waves by the measurement multiplexed light irradiated from this optical multiplexer 8.

The acoustic wave detector 11 detects acoustic waves generated from the measurement object 10, and converts the acoustic waves into photoacoustic signals of intensity proportionate to the sound pressure. For example, a microphone or piezoelectric element can be used for the acoustic wave detector 11.

The phase detection amplifier 12 amplifies the photoacoustic signals converted by the acoustic wave detector 11.

The waveform observer 13 observes the photoacoustic signals output from the phase detection amplifier 12, and sends observation results thereof to the recorder 14.

For example, in a case of a constant voltage/current source (omitted from illustration) supplying voltage to the first drive circuit 6 and second drive circuit 7, the measurement object 10 is irradiated by the measurement multiplexed light (λ1+λ2). With the intensity of photoacoustic signals generated by light of the wavelength λ1 represented by A1, and the intensity of photoacoustic signals generated by light of the wavelength λ2 represented by A2, the waveform observer 13 measures photoacoustic signals (A1+A2) of the same phase, by detecting measurement acoustic waves generated by the measurement multiplexed light. Note that the phase detection amplifier 12 may perform detection and amplification of the photoacoustic signals, in addition to the waveform observer 13 as in the present embodiment, and perform observation of the amplitude and phase of electric signals.

The recorder 14 calculates the concentration in blood of glucose that is the target component 10G, in the living organism that is the measurement object 10, on the basis of measurement results of photoacoustic signals sent from the waveform observer 13. More specifically, the recorder 14 has databases of absorbance spectra of water which is the background component 10W, absorbance spectra of components in living organisms, and absorbance spectra of the target component 10G at different concentrations. The recorder 14 computes the concentration of glucose that is the target component 10G, from the amplitude and phase of electric signals acquired as measurement results, on the basis of these databases. Note that details of computation processing by the recorder 14 will be described later.

The recorder 14 also performs control of the oscillator 4 and so forth via the waveform observer 13. The recorder 14 decides and assigns the wavelengths λ1 and λ2 of light output from the first light source 2 and second light source 3. In the present embodiment, the recorder 14 can perform comprehensive control of the component concentration measurement device 1.

Figure 2:
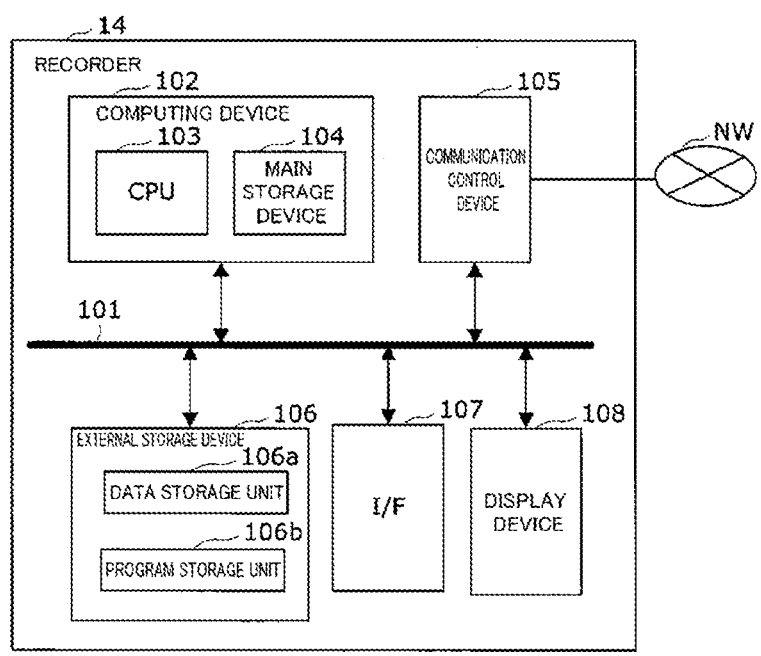
FIG. 2 is a block diagram illustrating a configuration example of a computer that realizes a recorder according to the embodiment of the present invention.

FIG. 2 is a block diagram illustrating a configuration example of a computer that realizes the recorder 14.

The recorder 14 can be realized by a computer that has a computing device 102 including a CPU 103 and a main storage device 104, a communication control device 105, an external storage device 106, an I/F 107, a display device 108, and so forth, which are connected via a bus 101, and a program that controls these hardware resources.

The CPU 103 and main storage device 104 make up the computing device 102. Programs for the CPU 103 to perform various types of control and computation are stored in the main storage device 104 beforehand.

The communication control device 105 is a control device for connecting between the recorder 14 and various types of external electronic equipment via a communication network NW. The communication control device 105 may calculate the concentration of the target component 10G in the measurement object 10, and transmit the calculated concentration to external equipment and the like via the communication network NW.

The external storage device 106 is configured of a read/writable storage medium, and a drive device that reads and writes various types of information, such as programs, data, and so forth, from and to the storage medium. A hard disk, semiconductor memory such as flash memory, or the like, can be used as storage media for the external storage device 106. The external storage device 106 may have storage devices or the like to perform backup of programs, data, and so forth, stored in the external storage device 106, for example, by a data storage unit 106a, a program storage unit 106b, and other such storage devices omitted from illustration.

The data storage unit 106a stores photoacoustic signals observed at the waveform observer 13. The data storage unit 106a also stores data of absorbance spectra of water, absorbance spectra of glucose, and absorbance spectra of the target component 10G at different absorbances.

The program storage unit 106b stores various types of programs for executing computation processing necessary for concentration conversion of the target component 10G and so forth in the present embodiment.

The I/F 107 is an interface for connecting the recorder 14 to other equipment included in the component concentration measurement device 1. The recorder 14 acquires observation results from the waveform observer 13 via the I/F 107.

The display device 108 makes up a display screen of the recorder 14. The display device 108 is realized by a liquid crystal display or the like. The display device 108 can display measurement values, such as concentration of the target component 10G acquired by the recorder 14, and so forth.

Note that in the component concentration measurement device 1 according to the present embodiment, the waveform observer 13 and so forth are also realized by hardware made up of a processor and storage device similar to the recorder 14, and programs that realize the functions thereof in collaboration with these pieces of hardware.

Operations of Concentration Measurement Device

Operations of the component concentration measurement device 1 having the above-described configuration will be described by way of a flowchart in FIG. 3.

A measurement object 10 such as an earlobe or finger or the like of a person is positioned between the light emission unit 9 and acoustic wave detector 11 beforehand. First, the waveform observer 13 acquires photoacoustic signals S1-1 while sweeping the wavelength of the first light source 2 (step S1). The acquired photoacoustic signals S1-1 are sent to the recorder 14 and stored in the data storage unit 106a.

Next, the waveform observer 13 acquires photoacoustic signals S2-1 while sweeping the wavelength of the second light source 3 (step S2). The acquired photoacoustic signals S2-1 are sent to the recorder 14 and stored in the data storage unit 106a.

Next, the temperature of the measurement object 10 is raised by a predetermined temperature $\Delta T$, by a heating mechanism (omitted from illustration) (Step S3). Thereafter, the waveform observer 13 acquires photoacoustic signals $S_{1-2}$ while sweeping the wavelength of the first light source 2 (step S4). The acquired photoacoustic signals $S_{1-2}$ are sent to the recorder 14 and stored in the data storage unit 106a.

Next, the waveform observer 13 acquires photoacoustic signals $S_{2-2}$ while sweeping the wavelength of the second light source 3 (step S5). The acquired photoacoustic signals $S_{2-2}$ are sent to the recorder 14 and stored in the data storage unit 106a.

Thereafter, the recorder 14 decides the combination of the wavelength $\lambda 1$ of the first light source 2 and the wavelength $\lambda 2$ of the second light source 3 (step S6). More specifically, the recorder 14 decides the values of the wavelengths $\lambda 1$ and $\lambda 2$ so that the relation of the photoacoustic signals acquired in the respective steps S1, S2, S4, and S5 is $(S_{1-1}-S_{2-1})=-(S_{2-2}-S_{2-1})$. The recorder 14 stores the values of the wavelengths $\lambda 1$ and $\lambda 2$ that have been decided in the data storage unit 106a.

Thereafter, the recorder 14 assigns the wavelengths $\lambda 1$ and $\lambda 2$ to the first light source 2 and second light source 3, respectively (step S7). Next, the waveform observer 13 acquires photoacoustic signals using the first light source 2 and second light source 3 to which the wavelengths $\lambda 1$ and $\lambda 2$ have been assigned (step S8).

More specifically, the first drive circuit 6 and second drive circuit 7 drive the first light source 2 and second light source 3 on the basis of modulation signals output from the oscillator 4, so that continuous light of the respective wavelengths $\lambda 1$ and $\lambda 2$ is output. Note that the light that the first light source 2 and second light source 3 output is of the same phase, as described above.

The output light is multiplexed by the optical multiplexer 8 via the optical fiber OF, and is emitted from the light emission unit 9 to the measurement object 10 as measurement multiplexed light. The living organism that is the measurement object 10 generates acoustic waves by the measurement multiplexed light irradiated from the optical multiplexer 8 via the light emission unit 9.

The acoustic wave detector 11 detects acoustic waves (photoacoustic waves) being generated from the living organism, and converts the acoustic waves into photoacoustic signals of intensity proportionate to the sound pressure. Thereafter, the phase detection amplifier 12 amplifies the photoacoustic signals converted by the acoustic wave detector 11. The photoacoustic signals output from the phase detection amplifier 12 are acquired by the waveform observer 13.

Next, the waveform observer 13 acquires photoacoustic signals in the same way, using only the first light source 2 to which the wavelength $\lambda 1$ is assigned (step S9). The acquired photoacoustic signals are sent to the recorder 14, and stored in the data storage unit 106a.

Thereafter, the waveform observer 13 detects photoacoustic waves where the wavelength $\lambda 1$ of the first light source has been shifted by a predetermined change amount $\Delta \lambda$, on the basis of control signals from the recorder 14 (step S10). The detected photoacoustic waves are sent to the recorder 14 and stored in the data storage unit 106a.

The recorder 14 then calculates a proportionality coefficient $F(t_i)$ that indicates the effects of acoustic resonance within the measurement object 10, i.e., change in the amplitude and phase of the acquired photoacoustic signals, using the following Expressions (1) (step S11).

Formula 3

$$F(t_0) = \frac{S^{\lambda_1+\Delta\lambda}(t_0) - S^{\lambda_1}(t_0)}{\Delta \alpha I} = \frac{Z(t_0)}{\Delta \alpha I} \quad (1)$$

$$F(t_1) = \frac{S^{\lambda_1+\Delta\lambda}(t_1) - S^{\lambda_1}(t_1)}{\Delta \alpha I} = \frac{Z(t_1)}{\Delta \alpha I}$$

In the above Expressions (i), $t_0$ and $t_1$ represent measurement clock times, and S represents photoacoustic signals. Also, $\alpha$ represents absorbance, and I represents optical power to be irradiated. Note that detailed description regarding the above Expressions (1) will be given later.

Thereafter, the recorder 14 uses the proportionality coefficient $F(t_i)$ calculated in step S11 to obtain a concentration change $\Delta C$ of glucose, for the target component 10G contained in the measurement object 10, by the following Expression (2) (step S12).

Formula 4

$$\Delta C(t) = \left(\frac{S_{12}(t_1)}{Z(t_1)} - \frac{S_{12}(t_0)}{Z(t_0)}\right)\frac{\Delta\alpha}{\gamma_{12}} \propto \left(\frac{S_{12}(t_1)}{Z(t_1)} - \frac{S_{12}(t_0)}{Z(t_0)}\right) \quad (2)$$

In the above Expression (2), $\gamma_{12}$ represents the temperature absorbance of the measurement object 10. Note that detailed description regarding the above Expression (2) will be given later.

Thereafter, the concentration change of glucose is obtained at each measurement clock time $t_i$ (i=0, 1, ..., n−1) (step S13: YES). Note that more specifically, the recorder 14 obtains the glucose concentration regarding the obtained concentration change by referencing a database stored beforehand. Thus, the component concentration measurement device normalizes the concentration change $\Delta C$ of glucose that is the target component 10G, using the above Expressions (1) and (2), to eliminate the effects of resonance of sound in the measurement object 10.

Normalization of the concentration change $\Delta C$ of the target component 10G will now be described in further detail.

First, absorbance $\alpha$ and photoacoustic signals S are expressed in the following Expression (3).

Formula 5

$$S = F(t) \cdot (\alpha + \beta \Delta T + \gamma \Delta C) \cdot I \quad (3)$$

In the above Expression (3), $\beta$ represents the molar absorbance of the target component 10G contained in the measurement object 10, $\gamma$ is the temperature absorbance of the measurement object 10, $\Delta T$ represents the temperature of the measurement object 10, and $\Delta C$ represents the concentration of the target component 10G contained in the measurement object 10. F(t) is the proportionality coefficient at the measurement clock time t. Also, I represents optical power that is irradiated by the light source. Thus, the photoacoustic signals S are in a proportionate relation to $F(t) \cdot (\alpha + \beta \Delta T + \gamma \Delta C)$.

The proportionality coefficient F(t) including the optical power I in the above Expression (3) is a coefficient that changes, and is difficult to control or predict. This proportionality coefficient F(t) is an unknown that is dependent on, for example, acoustic coupling of the acoustic wave detector 11 in the component concentration measurement device 1 and the measurement object 10, sensitivity of the acoustic wave detector 11, distance between the light emission unit 9 and measurement object 10, specific heat of the measurement object 10, thermal expansion coefficient of the measurement object 10, speed of sound at the measurement object 10, oscillation frequency of the oscillator 4, and further the absorbance $\alpha$ as well.

The amplitude and phase of the photoacoustic signals are dependent on cavity size and the internal structure of the measurement object 10, due to acoustic resonance within the measurement object 10. Accordingly, change in these causes change in the amplitude and phase of the photoacoustic signals, which is a factor in quantitative error occurring in the concentration of the target component to be measured.

According, in the present embodiment, the proportionality coefficient F(t) is obtained by photoacoustic signals acquired at a predetermined wavelength. Specifically, superimposed photoacoustic signals $S^{\lambda_1} + S^{\lambda_2}$ of signals of the same phase that have been observed using the first light source 2 and second light source 3 are acquired. The superimposed photoacoustic signals $S^{\lambda_1} + S^{\lambda_2}$ are expressed by the following Expression (4).

Formula 6

$$\begin{aligned}S^{\lambda_1} + S^{\lambda_2} &= F(t) \cdot \cdot \{(\alpha_1 + \alpha_2) + (\beta_1 + \beta_2)\Delta T + (\gamma_1 + \gamma_2)\Delta C\} \cdot I \quad (4) \\ &= F(t) \cdot \cdot \{(\alpha_1 + \alpha_2) + (\gamma_1 + \gamma_2)\Delta C\} \cdot I\end{aligned}$$

Now, each coefficient of the above Expression (4) is expressed as in the following Expressions (5).

Formula 7

$$S_{12} = S^{\lambda_1} + S^{\lambda_2}$$

$$\gamma_{12} = \gamma_1 + \gamma_2$$

$$\beta_{12} = \beta_1 + \beta_2 = 0$$

$$\alpha_{12} = \alpha_1 + \alpha_2 \quad (5)$$

With the measurement clock time $t_0$ at which measurement was started as a reference clock time, photoacoustic signals $S_{12}$ are acquired when there is change equivalent to concentration $\Delta C$ of the target component 10G at measurement clock time $t_1$ which is an optional amount of time elapsed. The photoacoustic signals $S_{12}$ are expressed by the following Expressions (6).

Formula 8

$$S_{12}(t_0) = F(t_0) \cdot \{\alpha_{12}\} \cdot I$$

$$S_{12}(t_1) = F(t_1) \cdot \{\alpha_{12} + \gamma_{12}\Delta C\} \cdot I \quad (6)$$

Now, normalization in order to eliminate the effects of resonance of the photoacoustic signals will be considered.

Figure 3:
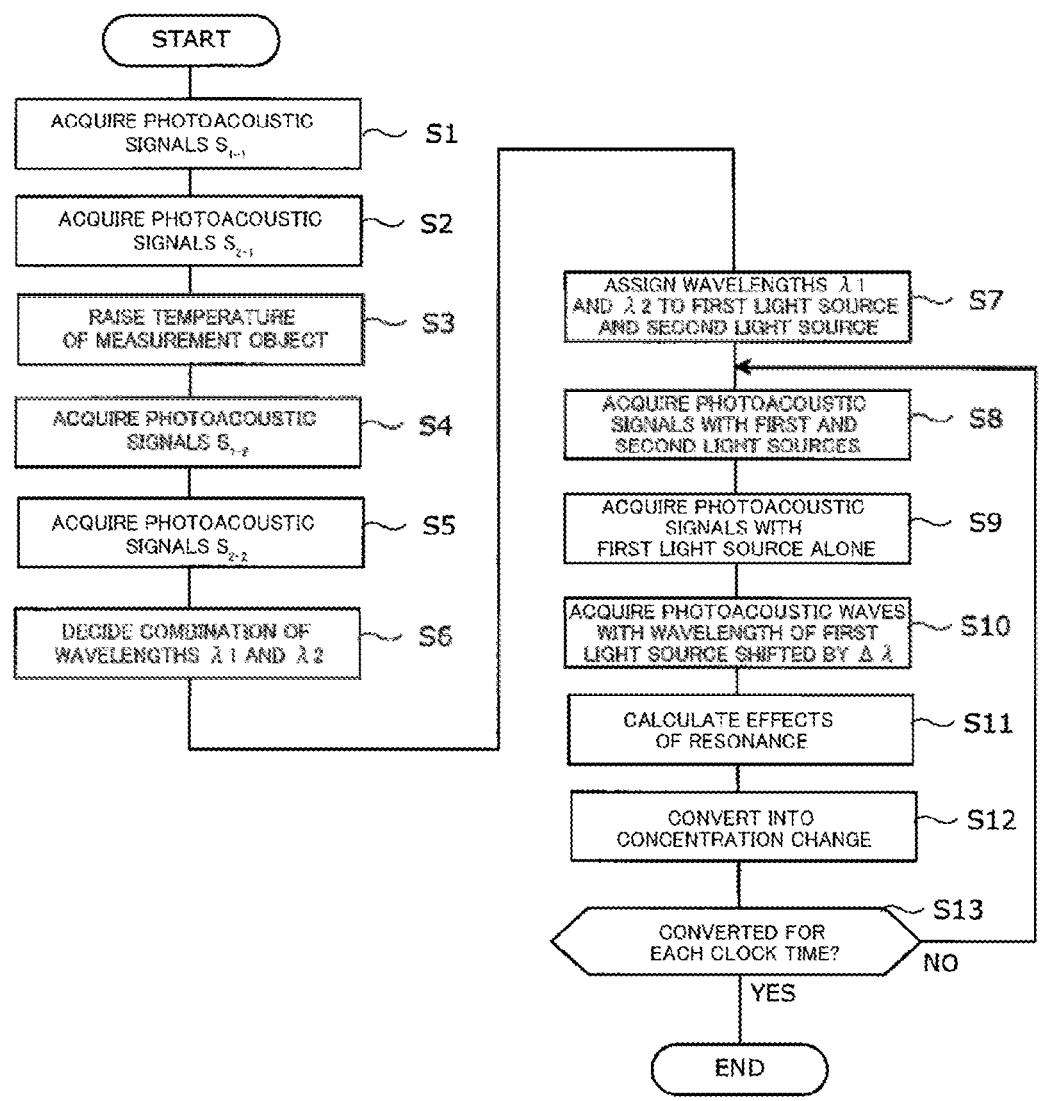
FIG. 3 is a flowchart for describing operations of the component concentration measurement device according to the embodiment of the present invention.

First, photoacoustic signals are acquired using only the light of the first light source 2 at clock time $t_0$ (FIG. 3, step S9), the measurement object 10 is irradiated by the first light source 2 with the wavelength having been shifted from the wavelength $\lambda 1$ by a change amount $\Delta\lambda$, and photoacoustic signals are acquired at this time (FIG. 3, step S10).

The photoacoustic signals before and after change of the wavelength $\lambda 1$ of light of the first light source 2 are expressed as in the following Expressions (7).

Formula 9

$$S^{\lambda_1}(t_0) = F(t_0) \cdot \{\alpha_1\} \cdot I$$

$$S^{\lambda_1}(t_1) = F(t_0) \cdot \{\alpha_1 + \gamma_1 \Delta C\} \cdot I$$

$$S^{\lambda_1 + \Delta\lambda}(t_0) = F(t_0) \cdot \{\alpha_1 + \Delta\alpha\} \cdot I$$

$$S^{\lambda_1 + \Delta\lambda}(t_1) = F(t_0) \cdot \{\alpha_1 + \gamma_1 \Delta C + \Delta\alpha\} \cdot I \quad (7)$$

Reorganizing the above Expressions (7) allows the proportionality coefficient $F(t_i)$ to be obtained regarding each measurement clock time $t_0$ and $t_1$, from Expressions (1).

Formula 10

$$F(t_0) = \frac{S^{\lambda_1 + \Delta\lambda}(t_0) - S^{\lambda_1}(t_0)}{\Delta\alpha I} = \frac{Z(t_0)}{\Delta\alpha I} \quad (1)$$

$$F(t_1) = \frac{S^{\lambda_1 + \Delta\lambda}(t_1) - S^{\lambda_1}(t_1)}{\Delta\alpha I} = \frac{Z(t_1)}{\Delta\alpha I}$$

Using these Expressions (1), the concentration change $\Delta C$ of the target component 10G can be obtained as in the following Expression (2).

Formula 11

$$\Delta C(t) = \left(\frac{S_{12}(t_1)}{Z(t_1)} - \frac{S_{12}(t_0)}{Z(t_0)}\right)\frac{\Delta\alpha}{\gamma_{12}} \propto \left(\frac{S_{12}(t_1)}{Z(t_1)} - \frac{S_{12}(t_0)}{Z(t_0)}\right) \quad (2)$$

The above procedures are executed for each measurement clock time $t_i$ (i=0, 1, ..., n−1) (FIG. 3, step S8 to step S13).

Figure 6:
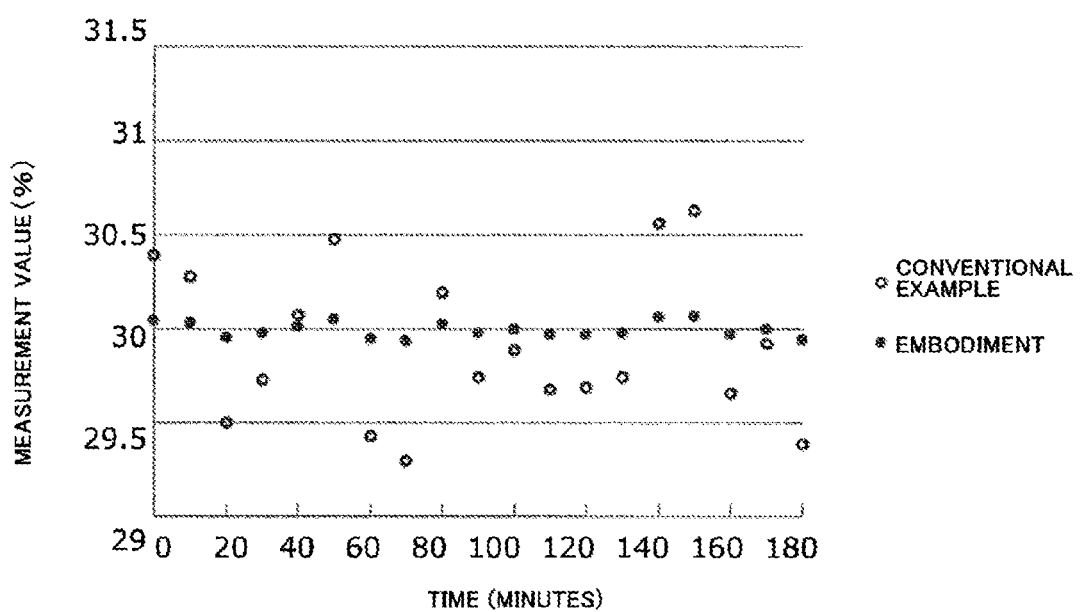
FIG. 6 is a diagram for describing effects of the component concentration measurement device according to the present embodiment.
Figure 7:
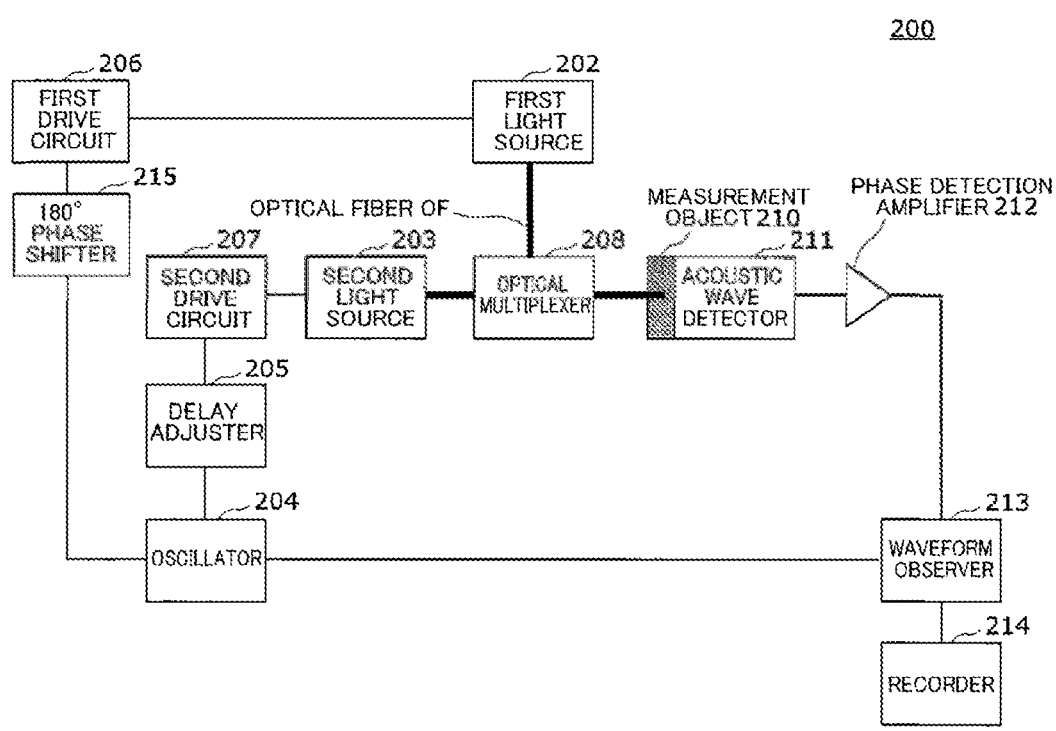
FIG. 7 is a block diagram illustrating a configuration example of a conventional component concentration measurement device.

Next, the effects of the component concentration measurement device 1 according to the present embodiment will be described by way of FIG. 6. The horizontal axis in FIG. 6 is measurement time, and the vertical axis represents the glucose concentration of the target component 10G. Also, the points indicated by "open circles" indicate the measurement results of the component concentration measurement device 200 according to the conventional example (FIG. 7). The points indicated by "filled-in circles" indicate the measurement results of the component concentration measurement device 1 according to the present embodiment.

More specifically, FIG. 6 illustrates the way in which measurement values fluctuate at the time of carrying out measurement at the environmental temperature without performing temperature control. It can be seen from FIG. 6 that the fluctuation of values is suppressed in the measurement values of the component concentration measurement device 1 according to the present embodiment in comparison with the measurement values of the component concentration measurement device 200 according to the conventional example. Accordingly, it can be understood that quantitative precision of measurement values of the concentration of the target component 10G improves with the component concentration measurement device 1 according to the present embodiment.

As described above, the component concentration measurement device 1 according to the present embodiment uses light of two wavelengths where light of wavelengths $\lambda 1$ and $\lambda 2$ from the first light source 2 and second light source 3 are of the same phase, and change in light absorption coefficient with regard to temperature is around the same with different signs from each other. Also, change in concentration of the target component 10G is normalized using a predetermined Expression, to eliminate the effects of resonance of photoacoustic signals. Accordingly, temperature dependency of absorbance of the background component is cancelled out, and accordingly quantitative precision of the concentration of components within living organisms can be improved.

Although an embodiment has been described above of the component concentration measurement device and component concentration measurement method of the present invention, the present invention is not limited to the described embodiment, and various modifications conceivable by one skilled in the art may be made within the scope of the invention set forth in the Claims.

For example, a case has been described in the present embodiment where the component concentration measurement device 1 is configured with the components thereof being connected to each other by electrical lines and optical fiber OF. However, part of the functional configuration of the component concentration measurement device 1 may be dispersedly located in a server on a network. For example, a configuration may be employed in which the waveform observer 13 and recorder 14 are provided in a server on a network.

Also, while description has been made in the present embodiment regarding a case where the component concentration measurement device 1 measures glucose concentration in blood in a living organism, this is not limited to glucose, as long as a component contained in a solution present in a human or animal.

REFERENCE SIGNS LIST

1 Component concentration measurement device
2 First light source
3 Second light source
4 Oscillator
5 Delay adjuster
6 First drive circuit
7 Second drive circuit
8 Optical multiplexer
9 Light emission unit
10 Measurement object
10G Target component
10W Background component
11 Acoustic wave detector
12 Phase detection amplifier
13 Waveform observer
14 Recorder
101 Bus
102 Computing device
103 CPU
104 Main storage device
105 Communication control device
106 External storage device
106a Data storage unit
106b Program storage unit
107 I/F
108 Display device

The invention claimed is:

1. A component concentration measurement device, comprising:
   a light irradiator that:
      performs intensity modulation on a first light by a first signal to obtain a first modulated light;
      performs intensity modulation on a second light by a second signal to obtain a second modulated light, wherein the first signal has a same frequency and a same phase as the second signal, and wherein the first light has a different wavelength than the second light;
      multiplexing the first modulated light and the second modulated light to obtain a multiplexed light; and
      irradiates a measurement object with the multiplexed light;
   a detector that:
      detects a photoacoustic wave generated within the measurement object due to irradiation by the light irradiator; and
      converts the photoacoustic wave into a first electric signal; and
   a processor that determines a concentration of a target component contained in the measurement object by comparing an amplitude of the first electrical signal and a phase of the first electric signal with absorbance spectra of one or more substances, wherein a first light absorption coefficient of the first light and a second light absorption coefficient of the second light corresponds to a background component contained in the measurement object and are equal in change amount with regard to a temperature change, and wherein the first light absorption coefficient has a sign different from the second light absorption coefficient.

2. The component concentration measurement device according to claim 1, wherein:
the light irradiator irradiates the measurement object by the first light where a first wavelength of the first light has been shifted by a predetermined change amount; and
the detector detects a first photoacoustic wave generated within the measurement object due to irradiation by the first light before the first wavelength of the first light is shifted by the predetermined change amount;
the detector detects a second photoacoustic wave generated within the measurement object due to irradiation by the first light after the first wavelength of the first light is shifted by the predetermined change amount;
the detector converts the first photoacoustic wave and the second photoacoustic wave into second electric signals; and
the processor normalizes the concentration of the target component contained in the measurement object based on the second electric signals.

3. The component concentration measurement device according to claim 2, wherein:
the processor calculates, at each measurement clock time of a plurality of measurement clock times, a respective proportionality coefficient for the first electric signal and a respective optical power of light by which the measurement object is irradiated by the light irradiator; and
the processor normalizes the concentration of the target component contained in the measurement object.

4. The component concentration measurement device according to claim 3, wherein the processor calculates the respective proportionality coefficient $F(t_i)$ at each measurement clock time $t_i$ based on:

$$F(t_i) = \frac{S^{\lambda_1 + \Delta\lambda}(t_i) - S^{\lambda_1}(t_i)}{\Delta \alpha I}$$

wherein $S^{\lambda_1}$ represents a signal of the second electric signals before the first wavelength is shifted by the predetermined change amount, $S^{\lambda_1 + \Delta\lambda}$ represents a signal of the second electric signals after the first wavelength is shifted by the predetermined change amount, $\Delta\alpha$ represents a change in absorbance, and I represents the respective optical power.

5. The component concentration measurement device according to claim 4, wherein:
the processor calculates a change $\Delta C(t)$ in concentration of the target component contained in the measurement object based on:

$$\Delta C(t) = \left( \frac{S_{12}(t_{i+n-1})}{Z(t_{i+n-1})} - \frac{S_{12}(t_i)}{Z(t_i)} \right) \frac{\Delta \alpha}{\gamma_{12}} \propto \left( \frac{S_{12}(t_{i+n-1})}{Z(t_{i+n-1})} - \frac{S_{12}(t_i)}{Z(t_i)} \right),$$
where $Z = S^{\lambda_1 + \Delta\lambda}(t) - S^{\lambda_1}(t)$, wherein $S_{12}$ represents the first electric signal detected based on the first light and the second light having been superimposed, wherein $\gamma_{12}$ represents a temperature absorbance of the measurement object, and wherein the change $\Delta C(t)$ in concentration of the target component contained in the measurement object is normalized.

6. The component concentration measurement device according to claim 1, wherein a first wavelength of the first light or a second wavelength of the second light is equal to a wavelength where an absorption of the target component is maximal.

7. A component concentration measurement method, comprising:
performing intensity modulation on a first light by a first signal to obtain a first modulated light;
performing intensity modulation on a second light by a second signal to obtain a second modulated light, wherein the first signal has a same frequency and a same phase as the second signal, and wherein the first light has a different wavelength than the second light; and
multiplexing the first modulated light and the second modulated light to obtain a multiplexed light;
irradiating a measurement object with the multiplexed light;
detecting a photoacoustic wave generated within the measurement object due to the measurement object being irradiated;
converting the photoacoustic wave into a first electric signal; and
obtaining a concentration of a target component contained in the measurement object by comparing an amplitude and a phase of the first electric signal with absorbance spectra of one or more substances, wherein a first light absorption coefficient of the first light and a second light absorption coefficient of the second light corresponds to a background component contained in the measurement object and are equal in change amount with regard to a temperature change, and wherein the first light absorption coefficient has a sign different from the second light absorption coefficient.

8. The component concentration measurement method according to claim 7, wherein:
the measurement object is irradiated by the first light where a first wavelength of the first light has been shifted by a predetermined change amount;
detecting the photoacoustic wave generated within the measurement object comprises:
detecting a first photoacoustic wave generated within the measurement object due to irradiation by the first light before the first wavelength of the first light is shifted by the predetermined change amount; and
detecting a second photoacoustic wave generated within the measurement object due to irradiation by the first light after the first wavelength of the first light is shifted by the predetermined change amount
converting the photoacoustic wave into the first electric signal comprises converting the first photoacoustic wave and the second photoacoustic wave into second electric signals; and
obtaining the concentration of the target component contained in the measurement object comprises normalizing the concentration of the target component contained in the measurement object based on the second electric signals.

9. The component concentration measurement method according to claim 8, wherein:
at each measurement clock time of a plurality of measurement clock times, calculating a respective proportionality coefficient for the first electric signal and a respective optical power of light by which the measurement object is irradiated; and normalizing the concentration of the target component contained in the measurement object.

10. The component concentration measurement method according to claim 9, wherein calculating the respective proportionality coefficient $F(t_i)$ at each measurement clock time $t_i$ comprises calculating the respective proportionality coefficient $F(t_i)$ based on:

$$F(t_i) = \frac{S^{\lambda_1 + \Delta\lambda}(t_i) - S^{\lambda_1}(t_i)}{\Delta\alpha I}$$

wherein $S^{\lambda_1}$ represents a signal of the second electric signals before the first wavelength is shifted by the predetermined change amount, $S^{\lambda_1 + \Delta\lambda}$ represents a signal of the second electric signals after the first wavelength is shifted by the predetermined change amount, $\Delta\alpha$ represents a change in absorbance, and I represents the respective optical power.

11. The component concentration measurement method according to claim 10, further comprising:

calculating a change $\Delta C(t)$ in concentration of the target component contained in the measurement object based on:

$$\Delta C(t) = \left( \frac{S_{12}(t_{i+n-1})}{Z(t_{i+n-1})} - \frac{S_{12}(t_i)}{Z(t_i)} \right) \frac{\Delta\alpha}{\gamma_{12}} \propto \left( \frac{S_{12}(t_{i+n-1})}{Z(t_{i+n-1})} - \frac{S_{12}(t_i)}{Z(t_i)} \right),$$

where $Z = S^{\lambda_1 + \Delta\lambda}(t) - S^{\lambda_1}(t)$, wherein $S_{12}$ represents the first electric signal detected based on the first light and the second light having been superimposed, wherein $\gamma_{12}$ represents a temperature absorbance of the measurement object, and wherein the change $\Delta C(t)$ in concentration of the target component contained in the measurement object is normalized.

12. The component concentration measurement method according to claim 7, wherein a first wavelength of the first light or a second wavelength of the second light is equal to a wavelength where an absorption of the target component is maximal.

\* \* \* \* \*